United States Patent [19]
Granger et al.

[11] Patent Number: 6,083,947
[45] Date of Patent: Jul. 4, 2000

[54] METHOD FOR TREATING SEXUAL DYSFUNCTIONS

[75] Inventors: Richard H. Granger; Gary S. Lynch, both of Irvine, Calif.

[73] Assignee: The Regents of the University of California, Oakland, Calif.

[21] Appl. No.: 08/787,005

[22] Filed: Jan. 28, 1997

Related U.S. Application Data

[60] Provisional application No. 60/010,778, Jan. 29, 1996, and provisional application No. 60/026,951, Sep. 17, 1996.

[51] Int. Cl.[7] .................................................... A01N 43/58
[52] U.S. Cl. .............................................. 514/249; 514/678
[58] Field of Search ...................................... 514/678, 249

*Primary Examiner*—Dwayne C. Jones
*Attorney, Agent, or Firm*—Townsend and Townsend and Crew LLP

[57] ABSTRACT

This invention is a novel treatment for sexual dysfunctions by administering to a subject exhibiting a sexual dysfunction compounds that upmodulate the AMPA receptor. Methods and compositions for treating sexual dysfunction are provided. Kits containing the compositions in appropriate form for administration are also provided.

33 Claims, 1 Drawing Sheet

FIGURE 1

METHOD FOR TREATING SEXUAL DYSFUNCTIONS

CROSS-REFERENCE TO RELATED APPLICATIONS

The present application is a continuation-in-part of U.S. provisional application Ser. No. 60/010,778, filed on Jan. 29, 1996, and U.S. provisional application Ser. No. 60/026,951, filed on Sep. 17, 1996, which are both incorporated by reference.

STATEMENT REGARDING FEDERALLY SPONSORED RESEARCH

The government may own certain rights in the present invention pursuant to Air Force Office of Scientific Research Grant F-49620-95-1-0304.

BACKGROUND OF THE INVENTION

The present invention relates to compositions and methods for treating sexual dysfunctions in mammalian subjects, particularly human males.

The DSM-IIIR defines four phases of sexual response (appetite, excitement, orgasm, resolution). Inhibition of any of these is collectively known as "sexual dysfunction." Sexual dysfunction in males specifically encompasses the inability to sustain a penile erection (Male Erectile Disorder or impotence), the inability to ejaculate and/or the inability to experience orgasm.

According to the DSM-III-R (p. 292), approximately 8% of young adult males have Male Erectile Disorder. An estimated 20% of the total population have Hypoactive Sexual Desire Disorder.

Male sexual dysfunction may be due to one or more causes.

About forty to sixty percent of cases of Male Erectile Disorder is associated with atherosclerosis of the arteries supplying blood to the penis ("arteriogenic" or "atherosclerotic" dysfunction). In some cases, there is leakage from veins in the penis such that sufficient pressure for an erection can neither be obtained nor maintained.

"Neurogenic" sexual dysfunction associated with a neuropathy (e.g., nerve damage in the nervous system affecting the penis arising from, for example, surgery or a pelvic injury) accounts for about ten to fifteen percent of impotence cases.

Psychological or "psychogenic" dysfunction, resulting, for example, from anxiety or depression, with no apparent substantial somatic or organic impairment, accounts for about fifteen to twenty percent of cases of impotence. These include an age-associated sexual decline which occurs unaccompanied by any overt pathologies.

Erectile insufficiency is sometimes a side effect of certain drugs, such as beta-blockers that are administered to reduce blood pressure in persons suffering from hypertension, or drugs administered to treat depression or anxiety. Excessive alcohol consumption is a cause of erectile insufficiency. These forms of sexual dysfunction may be regarded as a subset of neurogenic or psychogenic insufficiency.

In most cases, no hormonal or primarily structural (anatomical) defects are clinically demonstrable. This common type of impotence usually increases in frequency with advancing age. About twelve percent of adult men under age forty-five, about twenty percent of men at age sixty, and about fifty-five percent of men at age seventy-five experience difficulty in engaging in sexual intercourse.

A number of methods to treat sexual dysfunction are available. These treatments include surgery (e.g., penile implants), pharmacological treatments and, in cases of psychogenic dysfunction, psychological counseling. See, e.g., U.S. Pat. No. 5,399,581 to Laragh, Mar. 21, U.S. Pat. No. 5,439,007 to Fischer, Aug. 8, 1995, U.S. Pat. No. 5,447,912 to Gerstenberg et al., Sep. 5, 1995, U.S. Pat. No. 5,451,609 to Bellamy, Sep. 19, 1995, and references cited therein.

These published pharmacological methods of treatment have primarily targeted peripheral nervous system responses. They have had only limited success, and there are potentially severe side-effects.

Testosterone has been shown to be effective in modulating sexual behavior in a variety of mammals, including rats and humans. See, e.g., Smith et al. (1992), *Hormones and Behaviour* 26: 110–135 (rats) and Carani et al. (1990), *Arch. Sex. Behav.* 19: 223–234 (humans). However, steroid treatments have the potential for eliciting undesirable behaviors, for example, aggression.

Injection of or moxisylyte (ICAVEX) (U.S. Pat. No. 5,451,609 to Bellamy, Sep. 19, 1995), the smooth muscle relaxant papaverine, or the non-specific blocker and hypotensive phenoxybenzamine into a corpus cavernosum has been reported to cause an erection sufficient for vaginal penetration. Papaverine is effective in cases where the dysfunction is psychogenic or neurogenic and severe atherosclerosis is not involved.

In cases where severe atherosclerosis is not a cause of the dysfunction, intracavernosal injection of phentolamine, an alpha-adrenergic blocker, causes an erection that suffices for vaginal penetration. The resulting erection is one of significantly shorter duration than that induced by intracavernosal injection of papaverine or phenoxybenzamine. It often is of such short duration that satisfactory sexual relations are difficult or impossible.

The neuropeptide vasoactive intestinal peptide ("VIP") is thought to be associated with erections in normal males (i.e., males not suffering from erectile insufficiency). Injection of VIP into a corpus cavernosum of a normal male without subjecting the male to sexual stimulation causes slight swelling (slight tumescence) of the penis but not an erection. When coupled with visual sexual stimulation or sexual stimulation by vibration or both, injection of small amounts of VIP into a corpus cavernosum of a normal male facilitates full erection (see, Wagner et al. (1987) *World J. Urol.* 5: 171–172). VIP alone or coupled with sexual stimulation does not induce erections in males whose impotence is due to severe atherosclerosis.

It will be readily apparent that such invasive treatments require of the patient a great sense of purpose and a single-minded dedication to the task at hand, and that they may actually hinder rather than facilitate sexual activity. Intracavernosal injection is often associated with a burning sensation after the injection. In addition, papaverine or phenoxybenzamine can result in priapism, a persistent erection lasting from a few hours to sometimes longer than twenty-four hours. Priapism is a serious side effect of treatment of erectile insufficiency with these drugs. Beyond the embarrassment that some men may experience, priapism is often painful, can irreversibly damage erectile tissue, and, to be relieved, requires bleeding or pharmacological intervention, such as injection of a sympathomimetic drug such as adrenaline. There are indications that repeated use of papaverine causes extensive intracavernous fibrosis.

In summary, although sexual dysfunction is a pervasive problem, there are few satisfactory methods available for treating this disorder. Therefore, it is an object herein to provide methods and compositions for treating sexual dysfunctions.

SUMMARY OF THE INVENTION

The present invention is based on the discovery that male sexual dysfunction can be treated by compounds that enhance glutamatergic neural transmission. The invention comprises methods, compositions and kits for treating sexual dysfunctions in a subject in need thereof by up-modulating the stimulatory effect of natural ligands of α-amino-3-hydroxy-5-methyl-isoxazole-4-propionic acid ("AMPA") receptors.

A number of glutamatergic up-modulators may be used in the present invention; for example, 7-chloro-3-methyl-3-4-dihydro-2H-1,2,4 benzothiadiazine S,S, dioxide. In a preferred embodiment, the invention comprises administering to a subject an effective amount of a compound having the following formula (with ring vertices numbered as shown):

in which:

$R^1$ is a member selected from the group consisting of N and CH;

m is 0 or 1;

$R^2$ is a member selected from the group consisting of $(CR^8{}_2)_{n-m}$ and $C_{n-m}R^8{}_{2(n-m).2}$, in which n is 4, 5, 6, or 7, the $R^8$'s in any single compound being the same or different, each $R^8$ being a member selected from the group consisting of H and $C_1$–$C_6$ alkyl, or one $R^8$ being combined with either $R^3$ or $R^7$ to form a single bond linking the no. 3' ring vertex to either the no. 2 or the no. 6 ring vertices or a single divalent linking moiety linking the no. 3' ring vertex to either the no. 2 or the no. 6 ring vertices, the linking moiety being a member selected from the group consisting of $CH_2$, $CH_2$—$CH_2$, CH=CH, O, NH, N($C_1$–$C_6$ alkyl), N=CH, N=C ($C_1$–$C_6$ alkyl), C(O), O—C(O), C(O)—O, CH(OH), NH—C(O), and N($C_1$–$C_6$ alkyl)—C(O);

$R^3$, when not combined with any $R^8$, is a member selected from the group consisting of H, $C_1$–$C_6$ alkyl, and $C_1$–$C_6$ alkoxy;

$R^4$ is either combined with $R^5$ or is a member selected from the group consisting of H, OH, and $C_1$–$C_6$ alkoxy;

$R^5$ is either combined with $R^4$ or is a member selected from the group consisting of H, OH, $C_1$–$C_6$ alkoxy, amino, mono($C_1$–$C_6$ alkyl)amino, di($C_1$–$C_6$ alkyl) amino, and $CH_2OR^9$, in which $R^9$ is a member selected from the group consisting of H, $C_1$–$C_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of $C_1$–$C_3$ alkyl, $C_1$–$C_3$ alkoxy, hydroxy, halo, amino, alkylamino, dialkylamino, and methylenedioxy;

$R^6$ is either H or $CH_2OR^9$;

$R^4$ and $R^5$, when combined, form a member selected from the group consisting of in which:

$R^{10}$ is a member selected from the group consisting of O, NH and N($C_1$–$C_6$ alkyl);

$R^{11}$ is a member selected from the group consisting of O, NH and N($C_1$–$C_6$ alkyl);

$R^{12}$ is a member selected from the group consisting of H and $C_1$–$C_6$ alkyl, and when two or more $R^{12}$'s are present in a single compound, such $R^{12}$'s are the same or different;

p is 1, 2, or 3; and q is 1 or 2; and $R^7$, when not combined with any $R^8$, is a member selected from the group consisting of H, $C_1$–$C_6$ alkyl, and $C_1$–$C_6$ alkoxy.

Typical dosages for systemic administration can range from milligrams to decigrams per kg weight of subject per administration. Preferably, the glutamatergic drug used has a rapid onset and short half-life (≦90 min.)

In certain embodiments, methods are provided for treating a sexual dysfunction that is substantially psychogenic in origin. Preferentially, the human patient is one that has a reduced sexual drive, arousal or desire, age-associated hyposexuality, unaccompanied by other pathological anatomical indications or difficulties in reaching erection and/or orgasm. The methods of the invention reduce intromission latency and ejaculatory latency and promote erections sufficient for vaginal penetration in male mammals suffering from sexual dysfunctions that are predominantly psychogenic in nature. However, these methods are also effective to treat psychogenic symptoms in individuals whose sexual dysfunction is partly neurogenic or due to peripheral pathologies. These methods involve administering to the male a physiologically acceptable composition that contains an effective amount of glutamatergic compounds, and sexually stimulating the male.

Kits containing the compositions in the form of tablets or ampules or other suitable packaging means, formulated for controlled dosage administration, are also provided.

DETAILED DESCRIPTION OF THE INVENTION

Sexual behaviour generally comprises arousal (excitement), courtship displays, erotic manipulation, intercourse, orgasm and resolution. All of these are affected by neural and hormonal circuitries. The neural circuits involve central neural system and peripheral nervous system components.

Two principal elements of the male repertoire of sexual activity are erection and ejaculation. The first element, erection, is thought to be mediated by the parasympathetic nervous system. Cholinergic impulses from the spinal cord cause arterial dilatation and venous constriction in the penis. The arterial blood in the erectile tissue of the penis builds up under high pressure due to the venous constriction which blocks the outflow of blood from the penis. The second element, ejaculation, is thought to be mediated by the sympathetic nervous system. Sensory nerves in the penis respond to sexual stimulation by sending sensory impulses to the spinal cord. After processing these impulses, the spinal cord sends sympathetic impulses to the male reproductive organs, causing them to contract. This contraction results in the filling of the internal urethra with sperm and prostatic fluid. The corresponding pressure increase in the internal urethra stimulates pressure receptors which send impulses to the spinal cord. Cholinergic impulses are then sent from the spinal cord to the penis where the skeletal muscle surrounding the erectile tissue is stimulated to contract, causing ejaculation of the sperm from the internal urethra.

Existing approaches to treat male sexual dysfunction typically involve hormones and lower brain function. Much recent activity in sexual therapy has been aimed at the peripheral nervous system ("PNS"), largely because these systems are better understood. These approaches have yielded limited clinical success.

There is evidence that there is significant central nervous system ("CNS") participation in most instances of sexual performance deficits. For example, involvement of the striatal complex (nucleus accumbens septi) and the frontal cortex has been reported in sexual behavior (Robertson et al., 1991).

Most excitatory neurotransmission in these and other forebrain structures occurs via glutamate. The majority of CNS glutamatergic receptors are of the AMPA class. The remaining are of the NMDA class. See, Jonas, P., 1993, *Exs*, 66:61–76; Zorumsky et al., 1993, *Pharmacology and Therapeutics*, 59:145–162; and Orrego et al., 1993, *Neuroscience*, 56:539–555.

Facilitation of central (brain) glutamatergic transmission via up-modulation of "AMPA-type" glutamate receptors has larger effects on complex, polysynaptic circuitries than on simple circuits (Sirvio et al., 1995), and hence is expected to produce greater facilitation of the types of network functions found in neocortex than those located in the lower brain. From this perspective, centrally active up-modulators of the AMPA receptors should enhance the cortical component of elaborate behaviors, including sexual interactions, while minimally altering lower brain visceral activities.

The glutamatergic enhancers of this invention have as one target CNS pathways that underlie both sexual interest (libido, desire) and sexual function (arousal, copulation, orgasm). In brief, stimulated presynaptic neurons release neurotransmitters such as glutamate into the synaptic cleft. The neurotransmitter binds to receptors present on the postsynaptic neuron. The formation of the ligand-receptor complex results in the opening of ion channels which permit the passage of ions across the neural plasma membrane of the post-synaptic neuron. If the net flux of ions exceeds a certain threshold level, the postsynaptic neuron is stimulated.

The compounds of the present invention primarily act, not by directly stimulating neural activation, but by upmodulating ("allosteric modulation") neural activation and transmission in neurons that contain glutamatergic receptors. These compounds bind to the glutamate receptor at a site other than the glutamate binding site, but such binding does not by itself give rise to ion fluxes. However, when a glutamate molecule binds to a glutamate receptor that has bound to it a glutamatergic compound of the invention, the subsequent ion flux is of much longer duration. Thus, in the presence of the compounds used herein, postsynaptic neurons are activated by much lower concentrations of glutamate than postsynaptic neurons that do not contain bound compounds.

A. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

"Cyano" refers to the group —CN.

"Halogen" or "halo" refers to fluorine, bromine, chlorine, and iodine atoms.

"Hydroxy" refers to the group —OH.

"Thiol" or "mercapto" refers to the group —SH.

"Sulfamoyl" refers to the —SO$_2$NH$_2$.

"Alkyl" refers to a cyclic, branched or straight chain, alkyl group of one to eight carbon atoms. The term "alkyl" includes reference to both substituted and unsubstituted alkyl groups. This term is further exemplified by such groups as methyl, ethyl, n-propyl, i-propyl, n-butyl, t-butyl, i-butyl (or 2-methylpropyl), cyclopropylmethyl, cyclohexyl, i-amyl, n-amyl, and hexyl. Substituted alkyl refers to alkyl as just described including one or more functional groups such as aryl, acyl, halogen, hydroxyl, amido, amino, acylamino, acyloxy, alkoxy, cyano, nitro, thioalkyl, mercapto and the like. These groups may be attached to any carbon atom of the lower alkyl moiety. "Lower alkyl" refers to $C_1$–$C_6$ alkyl, with $C_1$–$C_4$ alkyl more preferred. "Cyclic alkyl" includes both mono-cyclic alkyls, such as cyclohexyl, and bi-cyclic alkyls, such as [3.3.0]bicyclooctane and [2.2.1] bicycloheptane. "Fluoroalkyl" refers to alkyl as just described, wherein some or all of the hydrogens have been replaced with fluorine (e.g., —CF$_3$ or —CF$_2$CF$_3$).

"Aryl" or "Ar" refers to an aromatic substituent which may be a single ring or multiple rings which are fused together, linked covalently, or linked to a common group such as an ethylene or methylene moiety. The aromatic ring(s) may contain a heteroatom, such as phenyl, naphthyl, biphenyl, diphenylmethyl, 2,2-diphenyl-1-ethyl, thienyl, pyridyl and quinoxalyl. The term "aryl" or "Ar" includes reference to both substituted and unsubstituted aryl groups. If substituted, the aryl group may be substituted with halogen atoms, or other groups such as hydroxy, cyano, nitro, carboxyl, alkoxy, phenoxy, fluoroalkyl and the like. Additionally, the aryl group may be attached to other moieties at any position on the aryl radical which would otherwise be occupied by a hydrogen atom (such as 2-pyridyl, 3-pyridyl and 4-pyridyl).

The term "alkoxy" denotes the group —OR, where R is lower alkyl, substituted lower alkyl, aryl, substituted aryl, aralkyl or substituted aralkyl as defined below.

The term "acyl" denotes groups —C(O)R, where R is alkyl, substituted alkyl, alkoxy, aryl, substituted aryl, amino and alkylthiol.

"Carbocyclic moiety" denotes a ring structure in which all ring vertices are carbon atoms. The term encompasses both single ring structures and fused ring structures. Examples of aromatic carbocyclic moieties are phenyl and naphthyl.

"Heterocyclic moiety" denotes a ring structure in which one or more ring vertices are atoms other than carbon atoms, the remainder being carbon atoms. Examples of non-carbon atoms are N, O, and S. The term encompasses both single ring structures and fused ring structures. Examples of aromatic heterocyclic moieties are pyridyl, pyrazinyl, pyrimidinyl, quinazolyl, isoquinazolyl, benzofuryl, isobenzofuryl, benzothiofuryl, indolyl, and indolizinyl.

The term "amino" denotes the group NRR', where R and R' may independently be hydrogen, lower alkyl, substituted lower alkyl, aryl, substituted aryl as defined below or acyl.

The term "amido" denotes the group —C(O)NRR', where R and R' may independently be hydrogen, lower alkyl, substituted lower alkyl, aryl, substituted aryl as defined below or acyl.

The term "independently selected" is used herein to indicate that the two R groups, $R^1$ and $R^2$, may be identical or different (e.g., both $R^1$ and $R^2$ may be halogen or, $R^1$ may be halogen and $R^2$ may be hydrogen, etc.).

A "sexual dysfunction" generally denotes the inhibition of any one or more of the phases of sexual response (appetite, excitement, orgasm, resolution) described in the DSM-IIIR. "Sexual dysfunction" specifically encompasses decreased sexual desire (Hypoactive Sexual Desire Disorder, DSM-lll-R #302.71), the inability to sustain a penile erection (Male Erectile Disorder, DSM-III-R #302.72), the inability to ejaculate and/or the inability to experience orgasm (Inhibited Male Orgasm, DSM-III-R #302.74). All may be psychogenic only, or psychogenic and biogenic, lifelong or acquired, and generalized or situational. The DSM-IIIR definitions and text relating to sexual dysfunction are hereby incorporated by reference.

"Impotence" or "Male Erectile Disorder" is the consistent inability to maintain an erect penis of sufficient rigidity for sexual intercourse.

"Sexual behavior" may or may not involve a partner. Where a partner is involved, sexual behavior comprises arousal, courtship displays and copulation. Arousal (or excitement) consists of a subjective sense of sexual pleasure and accompanying physiological changes. The major changes in the male comprise penile tumescence leading to erection. Courtship displays are behaviors intended to or having the effect of arousing a sexual partner and of increasing the arousal of the actor. Copulation may comprise intromission of the penis into the sexual partner's sexual organs (in heterosexual copulation), orgasm and ejaculation. Where a partner is not involved, sexual behavior may include any combination of touching or erotically manipulating erogenous areas of the genital organs or other erogenous parts of the body (e.g., masturbation); responding to visual stimulation such as pictorial depiction of erotic acts and objects.

The phrase "symptoms of sexual dysfunction" includes inhibition of any of the four phases of sexual response (appetite, excitement, orgasm, resolution) mentioned in the DSM-IIIR. These specifically include lack of sexual desire (Hypoactive Sexual Desire Disorder, DSM-III-R #302.71), impotence or the inability to sustain a penile erection (Male Erectile Disorder, DSM-III-R #302.72), the inability to ejaculate and/or the inability to experience orgasm (Inhibited Male Orgasm, DSM-III-R #302.74).

The phrase "diminish the symptoms of sexual dysfunction" denotes a decrease in the inhibition of any one or more of the four phases of sexual response (appetite, excitement, orgasm, resolution) described in the DSM-IIIR. The phrase specifically encompasses increased sexual desire, the enhanced ability to sustain a penile erection, the enhanced ability to ejaculate and/or to experience orgasm. A particular example of diminished symptoms of sexual dysfunction is an increase in the number, frequency and duration of instances of sexual behavior or of subjective sexual arousal.

The term "subject" means a male mammal, particularly a human. The term specifically includes domestic and common laboratory mammals, such as non-human primates, kine, horses, pigs, goats, sheep, rabbits, rats and mice.

"Age-related sexual dysfunctions" are sexual dysfunctions that are manifested in aging subjects and that often worsen with increasing age. They are common to both human and animal species (Davidson et al., 1983a; 1983b; Smith and Davidson, 1990).

"α-amino-3-hydroxy-5-methyl-isoxazole-4-propionic acid", or "AMPA", or "glutamatergic" receptors are molecules or complexes of molecules present in cells, particularly neurons, usually at their surface membrane, that recognize and bind to glutamate or AMPA. The binding of AMPA or glutamate to an AMPA receptor normally gives rise to a series of molecular events or reactions that result in a biological response. The biological response may be the activation or potentiation of a nervous impulse, changes in cellular secretion or metabolism, or causing cells to undergo differentiation or movement.

The term "central nervous system" or "CNS" comprises the brain and the spinal cord. The term "peripheral nervous system" or "PNS" comprises all parts of the nervous system that are not part of the CNS, including cranial and spinal nerves and the autonomic nervous system.

The phrase "effective amount" means a dosage sufficient to produce a desired result. Generally, the desired result is a subjective or objective decrease in the symptoms of sexual dysfunction, as measured by the techniques described below.

B. Compounds Used to Treat Sexual Dysfunction

Compounds useful in the practice of this invention are generally those which amplify (upmodulate) the activity of the natural stimulators of AMPA receptors, particularly by amplifying excitatory synaptic response. We describe herein a wide variety of diverse compounds suitable for use in the invention. Methods for identifying other compounds are routine. They involve a variety of accepted tests to determine whether a given candidate compound is an upmodulator of the AMPA receptor. The primary assay is measurement of enlargement of the excitatory postsynaptic potential (EPSP) in in vitro brain slices, such as rat hippocampal brain slices.

In experiments of this kind, slices of hippocampus from a mammal such as rat are prepared and maintained in an interface chamber using conventional methods. Field EPSPs are recorded in the stratum radiatum of region CA1b and elicited by single stimulation pulses delivered once per 20 seconds to a bipolar electrode positioned in the Schaffer-commissural projections (see Granger, R. et al., 1993, *Synapse*, 15:326–329; Staubli, U. et al., 1994a, *Proc. Nat. Acad. Sci.*, 91:777–781; and Staubli, V. et al., 1994b, *Proc. Nat. Acad. Sci.*, 91:11158–11162; Arai, A. et al., 1994, *Brain Res.*, 638:343–346; Arai, A. et al., "Effects of a centrally active drug on AMPA receptor kinetics).

The wave form of a normal EPSP is composed of:
an AMPA component, which has a relatively rapid rise time in the depolarizing direction (~5–10 msec) and which decays within ~20 msec.;
an NMDA component (slow ~30–40 msec rise time and slow ~40–70 msec decay) (the NMDA portion will not appear in normal CSF media, due to the voltage requirement for NMDA receptor channel activation, but in low magnesium media, an NMDA component may appear;

a GABA component in the opposite (hyperpolarizing) direction as the glutamatergic (AMPA and NMDA) components, exhibiting a time course with a rise time of ~10–20 msec and very slow decay (~50–100 msec or more).

The different components can be separately measured to assay the effect of a putative AMPA receptor enhancing agent. This is accomplished by adding agents that block the unwanted components, so that the detectable responses are essentially only AMPA responses. For example, to measure AMPA responses, an NMDA receptor blocker (e.g., AP-5 or other NMDA blockers known in the art) and/or a GABA blocker (e.g., picrotoxin or other GABA blockers known in the art) are added to the slice. To prevent epileptiform activity in the GABA-blocked slices, known agents such as tetrodotoxin may be used.

AMPA upmodulators useful in the present invention are substances that cause an increased ion flux through the AMPA receptor complex channels in response to glutamatergic stimulation. Increased ion flux is typically measured as one or more of the following non-limiting parameters: at least a 10% increase in decay time, amplitude of the waveform and/or the area under the curve of the waveform and/or a decrease of at least 10% in rise time of the waveform, for example in preparations treated to block NMDA and GABA components. The increase or decrease is preferably at least 25–50%; most preferably it is at least 100%. How the increased ion flux is accomplished (e.g., increased amplitude or increased decay time) is of secondary importance; upmodulation is reflective of increased ion fluxes through the AMPA channels, however achieved.

An additional and more detailed assay is that of excised patches, i.e., membrane patches excised from cultured hippocampal slices; methods are described in Arai et al., 1994. Outside-out patches are obtained from pyramidal hippocampal neurons and transferred to a recording chamber. Glutamate pulses are applied and data are collected with a patch clamp amplifier and digitized (Arai et al., 1994).

Because these membrane patches should contain only glutamatergic receptors, GABAergic currents will not be seen. Any NMDA currents can be blocked as above (e.g., with AP-5).

The central action of a drug can be verified by measurement of Field EPSPs in behaving animals (see Staubli et al., 1994a) and time course of biodistribution can be ascertained via injection and PET measurement of radiolabeled drug (see Staubli et al., 1994b).

One such class of compounds is defined by Formula I:

(I)

In this formula:
R$^1$ is either N or CH;
m is either 0 or 1;
R$^2$ is either $(CR^8{}_2)_{n-m}$ or $C_{n-m}R^8{}_{2(n-m)2}$, in which:
n is 4, 5, 6, or 7; and the R$^8$'s in any single compound are either the same or different, each R$^8$ being either H or C$_1$–C$_6$ alkyl, or one R$^8$ being combined with either R$^3$ or R$^7$ to form a single bond bridging the no. 3' and either the no. 2 or the no. 6 ring vertices or a single divalent linking moiety linking the no. 3' and either the no. 2 or the no. 6 ring vertices, examples of single divalent linking moieties being CH$_2$, CH$_2$—CH$_2$, CH=CH, O, NH, N(C$_1$–C$_6$ alkyl), N=CH, N=C(C$_1$–C$_6$ alkyl), C(O), O—C(O), C(O)—O, CH(OH), NH—C (O), and N(C$_1$–C$_6$ alkyl)—C(O);

R$^3$, when not combined with any R$^8$, is either H, C$_1$–C$_6$ alkyl, or C$_1$–C$_6$ alkoxy;

R$^4$ is either H, OH, or C$_1$–C$_6$ alkoxy, or is combined with R$^5$;

R$^5$ is either combined with R$^4$ or is H, OH, C$_1$–C$_6$ alkoxy, amino, mono(C$_1$–C$_6$ alkyl)amino, di(C$_1$–C$_6$ alkyl) amino, or CH$_2$OR$^9$, in which:
R$^9$ is H, C$_1$–C$_6$ alkyl, an aromatic carbocyclic moiety, an aromatic heterocyclic moiety, an aromatic carbocyclic alkyl moiety, an aromatic heterocyclic alkyl moiety, or any such moiety substituted with one or more members of the group C$_1$–C$_3$ alkyl, C$_1$–C$_3$ alkoxy, hydroxy, halo, amino, alkylamino, dialkylamino, and methylenedioxy;

R$^6$ is either H or CH$_2$OR$^9$;

R$^4$ and R$^5$ when combined form a member selected from the group consisting of in which:
R$^{10}$ is either O, NH or N(C$_1$–C$_6$ alkyl);
R$^{11}$ is either O, NH or N(C$_1$–C$_6$ alkyl);
R$^{12}$ is either H or C$_1$–C$_6$ alkyl, and when two or more R$^{12}$'s are present in a single compound, such R$^{12}$'s are the same or different;
p is 1, 2, or 3; and
q is 1 or 2; and
R$^7$, when not combined with any R$^8$, is either H, C$_1$–C$_6$ alkyl, or C$_1$–C$_6$ alkoxy.

Within the scope of Formula I, certain subclasses are preferred. One of these is the subclass in which R$^2$ is (CHR$^8$)$_{n-m}$ or C$_{n-m}$HR$^8{}_{2(n-m).3}$, and R$^3$ is H, C$_1$–C$_6$ alkyl, or C$_1$–C$_6$ alkoxy. Another is the subclass in which R$^2$ is (CHR$^8$)$_{n-m}$ or C$_{n-m}$HR$^8{}_{2(n-m).3}$, and one R$^8$ is combined with either R$^3$ or R$^7$ to form a single bond bridging the 2 and 3' ring vertices or a single divalent linking moiety linking the 2 and 3' ring vertices, with CH$_2$, CH$_2$—CH$_2$, CH=CH, O, NH, N(C$_1$–C$_6$ alkyl), N=CH, N=C(C$_1$–C$_6$ alkyl), C(O), O—C(O), C(O)—O, CH(OH), NH—C(O), or N(C$_1$–C$_6$ alkyl)—C(O) as the linking moiety. A preferred subclass of R$^2$ is CHR$^8$—CH$_2$—CH$_2$—CH$_2$ and CHR$^8$—CH$_2$—CH$_2$—CH$_2$—CH$_2$. A preferred subclass of linking moieties is CH$_2$, CH$_2$—CH$_2$, CH=CH, O, NH, C(O), and CH(OH). A further preferred subclass is CH$_2$, O, NH, C(O), and CH(OH).

When R$^4$ and R$^5$ are combined, a preferred subclass for R$^{12}$ is H and CH$_3$, and preferred groups representing the combination of R$^4$ and R$^5$ are and In these groups, $R^{10}$ and $R^{11}$ are both preferably O, and p is 1 or 2. Still further preferred subclasses are those in which m is zero.

A further class of compounds useful in the practice of the invention are those of Formula II:

II

In Formula II, $R^1$ and $R^2$ are independently selected and are functional groups including, but not limited to, the following: hydrogen, alkyl, alkoxy, —SO$_2$NH$_2$, —NO$_2$, cyano and halogen. $R^3$ is a functional group including, but not limited to, the following: alkyl, alkoxy, halogen, hydroxy, acyl, aryl, —NO$_2$ and —SO$_2$NH$_2$. Finally, $R^4$ is a functional group including, but not limited to, the following: hydrogen, alkyl, acyl and aryl. These compounds were prepared by Dr. Richard Chamberlain et al., and are described in U.S. provisional application Ser. No. 60/026,951, filed on Sep. 17, 1996, which is incorporated by reference.

Within the scope of Formula II, certain embodiments are preferred, namely those in which $R^1$ and $R^2$ are independently selected and are hydrogen, alkyl, alkoxy, —SO$_2$NH$_2$ or halogen. Equally preferred are embodiments in which $R^3$ is alkyl, alkoxy, acyl or aryl. Equally preferred are embodiments in which $R^4$ is alkyl, acyl or aryl. Even more preferred are embodiments in which $R^1$ is halogen; $R^2$ is hydrogen, —SO$_2$NH$_2$ or halogen; $R^3$ is alkyl, alkoxy, acyl and aryl; and $R^4$ is alkyl, acyl or aryl. Even more preferred are embodiments in which $R^1$ is halogen; $R^2$ is H; $R^3$ is alkyl and, in particular, lower alkyl; and $R^4$ is alkyl. Equally preferred are embodiments in which $R^1$ is hydrogen, alkyl or alkoxy; $R^2$ is hydrogen, alkyl or alkoxy; $R^3$ is alkyl, alkoxy or halogen; and $R^4$ is alkyl, acyl or aryl.

Also preferred is the embodiment in which $R^1$ is Cl; $R^2$ is H; $R^3$ is ethyl; and $R^4$ is methyl. Also preferred is the embodiment in which $R^1$ is methyl; $R^2$ is H; $R^3$ is methyl; and $R^4$ is methyl. Also preferred is the embodiment in which $R^1$ is H; $R^2$ is methyl; $R^3$ is methyl; and $R^4$ is methyl. Also preferred is the embodiment in which $R^1$ is ethyl; $R^2$ is H; $R^3$ is methyl; and $R^4$ is methyl. Also preferred is the embodiment in which $R^1$ is methoxy; $R^2$ is H; $R^3$ is methoxy; and $R^4$ is methyl. Also preferred is the embodiment in which $R^1$ is methyl; $R^2$ is H; $R^3$ is Cl; and $R^4$ is methyl. Also preferred is the embodiment in which $R^1$ is Cl; $R^2$ is H; $R^3$ is i-propyl; and $R^4$ is methyl. Also preferred is the embodiment in which $R^1$ is F; $R^2$ is H; $R^3$ is methyl; and $R^4$ is methyl.

Also preferred are compounds of Formula IIa

IIa

In Formula IIa:

$R^{21}$ is either H, halo or CF$_3$;

$R^{22}$ and $R^{23}$ either are both H or are combined to form a double bond bridging the 3 and 4 ring vertices;

$R^{24}$ is either H, C$_1$–C$_6$ alkyl, C$_5$–C$_7$ cycloalkyl, C$_5$–C$_7$ cycloalkenyl, Ph, CH$_2$Ph, CH$_2$SCH$_2$Ph, CH$_2$X, CHX$_2$, CH$_2$SCH$_2$CF$_3$, CH$_2$SCH$_2$CH=CH$_2$, or and $R^{25}$ is a member selected from the group consisting of H and C$_1$–C$_6$ alkyl.

Within the scope of Formula IIa, certain subclasses are preferred. One of these is the subclass in which $R^{21}$ is Cl or CF$_3$, with Cl preferred. Another is the subclass in which all X's are Cl. Still another is the subclass in which $R^{22}$ and $R^{23}$ are both H. A preferred subclass of $R^{24}$ is that which includes CH$_2$Ph, CH$_2$SCH$_2$Ph, and

Preferred compounds within the scope of Formula IIa are those in which $R^{24}$ is either C$_5$–C$_7$ cycloalkyl, C$_5$–C$_7$ cycloalkenyl or Ph ("Ph" denotes a phenyl group). Other preferred compounds of this group are those in which $R^{21}$ is halo, $R^{22}$ is H, $R^{23}$ is H, and $R^{25}$ is H. Preferred substituents for $R^{24}$ are cyclohexyl, cyclohexenyl, and phenyl.

Compounds 1 through 25 below are examples of compounds within the scope of Formula I:

1

-continued

| | |
|---|---|
| 2  | 7  |
| 3  | 8  |
| 4  | 9  |
| 5  | 10  |
| 6  | 11  |

12

13

14

15

16

17 aniracetam

18

19

20

21

Compounds 26 through 40 below are examples of compounds within the scope of Formula II.

A particularly preferred compound is compound CX 516, 1-(Quinoxalin-6-ylcarbonyl)piperidine, having the following structure:

1. Preparation of Formula I Compounds

The compounds described above can be prepared by conventional methods known to those skilled in the art of synthetic organic chemistry. For example, certain compounds of Formula I can be prepared from an appropriately substituted benzoic acid by contacting the acid under conditions suitable to activate the carboxy group for the formation of an amide. This is accomplished, for example, by activating the acid with carbonyl diimidazole, or with a chlorinating agent such as thionyl chloride or oxalyl chloride to obtain the corresponding benzoyl chloride. The activated acid is then contacted with a nitrogen-containing heterocyclic compound under conditions suitable for producing the desired imide or amide. Alternatively, the substituted benzoic acid can be ionized by contact with at least two equivalents of base such as triethylamine in an inert solvent such as methylene chloride or alcohol-free chloroform, and the ionized benzoic acid can then be reacted with pivaloyl chloride or a reactive carboxylic acid anhydride such as trifluoroacetic anhydride or trichloroacetic anhydride, to produce a mixed anhydride. The mixed anhydride is then contacted with a nitrogen-containing heterocyclic compound to produce the desired imide or amide.

A further alternative to these methods, suitable for some of the compounds of Formula I, is to contact the appropriately selected 3,4-(alkylenedihetero)-benzaldehyde with ammonia to form an imine, then contacting the imine with benzoyloxycarbonyl chloride to form the benzoyloxycarbonyl imine. Suitable 3,4-(alkylenedihetero)-benzaldehydes include 3,4-(methylenedioxy)-benzaldehyde, 3,4-(ethylenedioxy)-benzaldehyde, 3,4-(propylenedioxy)-benzaldehyde, 3,4-(ethylidenedioxy)-benzaldehyde, 3,4-(propylenedithio)-benzaldehyde, 3,4-(ethylidenedithio)-benzaldehyde, 5-benzimidazolecarboxaldehyde, and 6-quinoxalinecarboxaldehyde. The benzoyloxycarbonyl imine is then contacted with a simple conjugated diene such as butadiene under cycloaddition reaction conditions, and then with a Lewis acid under conditions suitable for a Friedel-Crafts acylation. Examples of suitable conjugated dienes include butadiene, 1,3-pentadiene, and isoprene, and examples of suitable Lewis acids include $AlCl_3$ and $ZnCl_2$.

Still further compounds within Formula I are prepared from 2,3-dihydroxy naphthalene. This starting material is reacted with 1,2-dibromoethane in the presence of base to produce an ethylenedioxy derivative of naphthalene, which is then reacted with an oxidizing agent such as potassium permanganate to produce 4,5-ethylenedioxyphthaldehydic acid. The latter is contacted with anhydrous ammonia to form an imine, which is then treated with a suitable carbonyl-activating agent such as dicyclohexylcarbodiimide under cyclization conditions to form an acyl imine. The acyl imine is then reacted with a simple conjugated diene to achieve cycloaddition.

Still further compounds within Formula I can be prepared by contacting an α-halotoluic acid with at least two equivalents of an alkali salt of a lower alcohol according to the Williamson ether synthesis to produce an ether linkage. The resulting alkoxymethylbenzoic acid is activated with carbonyidiimidazole, thionyl chloride, dicyclohexylcarbodiimide, or any other suitable activating agent, and reacted with a suitable amine to achieve a carboxamide linkage.

In an alternate to the scheme of the preceding paragraph, a formyl-substituted aromatic carboxamide is prepared by activation of an appropriate starting acid with a tertiary amine (for example, triethyl amine) plus an acid chloride (for example, pivaloyl chloride) to produce a mixed anhydride for coupling to a suitable amine. The formyl group is then reduced to an alcohol by a suitable reducing agent such as sodium borohydride. The alcohol is then converted to a leaving group which is replaceable by the alkali salt of an alcohol. The leaving group can be generated by reagents such as thionyl chloride, thionyl bromide, mineral acids such as hydrochloric, hydrobromic or hydroiodic acids, or the combined action of a tertiary amine plus either a suitable sulfonic anhydride or sulfonyl halide. Alternatively, the alcohol can be activated by removing the proton. This is achieved by the action of a strong base such as sodium hydride in an aprotic solvent such as dimethylformamide. The resulting alkoxide is then reacted with a suitable alkyl halide or other alkyl compound with a suitable leaving group to produce the desired ether linkage.

Fused ring structures such as those in which $R^3$ and one of the $R^8$'s of Formula I are combined to form a single linking group bridging the 2 and 3' carbon atoms can be synthesized in the following manner. The carboxyl group of an appropriately substituted salicylic acid is activated with carbonyldiimidazole in dichloromethane, chloroform, tetrahydrofuran, or other anhydrous solvent. An aminoalkylacetal such as $H_2N(CH_2)_3CH(OCH_2CH_3)_2$ is then added. The resulting amide is treated with an aryl or alkyl sulfonic acid, trifluoroacetic acid, or other strong acid, in a solvent of low basicity such as chloroform or dichloromethane, to cleave the acetal and cyclize the intermediate aldehyde with the amide nitrogen and the phenolic oxygen.

In all of these reaction schemes, the methods and reaction conditions for each of the individual reactions are well within the routine skill of, and will be readily apparent to, the synthesis chemist.

2. Preparation of Formula II and IIa Compounds

Compounds of Formula II and methods for their preparation are described in the literature. These methods are within the routine skill of the synthesis chemist. The preparation of compounds such as bendroflumethiazide, for example, is described by Goldberg (Squibb), in U.S. Pat. No. 3,265,573 (1966). The preparation of compounds such as benzthiazide, epithiazide, methalthiazide and polythiazide is described by McManus (Pfizer), U.S. Pat. No. 3,009,911 (1961). The preparation of buthiazide is described in U.K. Pat. Nos. 861,367 and 885,078 (Ciba, 1961). The preparation of chlorothiazide is described by Hinkley (Merck & Co.), U.S. Pat. Nos. 2,809,194 (1957) and 2,937,169 (1960). The preparation of hydrochlorothiazide is described by Novello (Merck & Co.), U.S. Pat. No. 3,025,292 (1962); de Stevens and Werner (Ciba), U.S. Pat. No. 3,163,645 (1964); and Irons et al. (Merck & Co.), U.S. Pat. No. 3,164,588 (1965). The preparation of hydroflumethiazide is described by Lund et al. (Lövens), U.S. Pat. No. 3,254,076 (1966). The preparation of methylclothiazide is described by Close et al., 1960, J. Am. Chem. Soc., 82:1132. The preparation of trichlormethiazide is described by de Stevens et al., 1960, Experientia, 16:113. The disclosures of each of these patents and papers is incorporated herein by reference.

The compounds of the Formula IIa can be synthesized in a variety of ways, using conventional synthetic chemistry techniques. Typically, the compounds of the present invention are prepared according to the following general reaction scheme:

wherein $R^1$, $R^2$ $R^3$ and $R^4$ are as defined above. The use of appropriate organic solvents, temperature and time conditions for running the reactions are within the level of skill in the art. Reactions of this type are generally described in Werner, et al., J. Am. Chem. Soc., 82:1161–1166 (1960); U.S. Pat. No. 3,288,678 issued to de Stevens, et al.; U.S. Pat. No. 3,40,150 issued to de Stevens, et al., the teachings of which are incorporated by reference.

Generally, the reaction is carried out as follows. A salt of the aniline derivative is used as the starting material and may be a salt with an alkali metal or an acid addition salt. Preferably, the aldehyde is reacted with the aniline derivative in about stoichiometric amounts and in the presence of a small amount of an acid, particularly a mineral acid, such as hydrohalic acid, e.g., hydrochloric or hydrobromic acid, or sulfuric acid, if desired, in anhydrous form. The aldehyde may also be given into the reaction medium in a form which yields the desired reactant in situ. Thus, for example, when formaldehyde is used as the reactant, it may be desirable to use it in the form of a polymer, such as paraformaldehyde or trioxane, or as an acetal, such as dimethoxymethane or diethoxymethane. Other aldehydes may be used as acetals, such as 1,1-di-methoxy-ethane or 1,1-diethoxy-ethane. The reaction may be carried out in the absence or preferably in the presence of a solvent, for example, an ether, e.g., p-dioxane or di-ethyleneglycol dimethylether, or a formamide, e.g., di-methylformamide. It may be completed at an elevated temperature, for example, at the boiling temperature of the solvent. Thus, the aldehyde reactant is, for example, added to a preheated solution of the aniline derivative in the solvent containing the acid and heating may then be continued to complete the reaction. If necessary, the reaction may be performed under increased pressure or in the atmosphere of an inert gas, e.g., nitrogen.

3. Screening of Compounds

A number of compounds belonging to the above-described genus have been shown to up-modulate glutamatergic transmission by augmenting ligand-AMPA receptor complex-activated ion gating. Staubli, U. et al., 1994a, Proc. Nat. Acad. Sci. U.S.A., 91:777–781; Staubli, U. et al., 1994b, Proc. Nat. Acad. Sci. U.S.A., 91:11158–11162; Arai, A. et al., 1994, Brain Res., 638:343–346; Granger, R. et al., 1993, Synapse, 15:326–329; all of which are incorporated by reference. These compounds rapidly cross the blood-brain barrier (Staubli, U. et aL, 1994b) and increase ESPSs in freely moving rats (Staubli, U. et al., 1994a).

Animal experiments indicate that these centrally active modulators improve memory in both rat (Granger, R. et al., 1993; Staubli, U. et al., 1994a) and human models (Lynch et al., 1996, *Internat. Clinical Psychopharmacology* 11:13; lngvar et al., submitted to *Science*, both of which are incorporated by reference).

Once prepared, the compounds of this invention can be screened for their ability to amplify (upmodulate) the activity of the natural stimulators of AMPA receptors, particularly by amplifying excitatory synaptic responses. A variety of accepted tests can be used to determine whether a given compound is an upmodulator of the AMPA receptor. The primary assay is measurement of the enlargement of the excitatory postsynaptic potential (EPSP) in in vitro brain slices, such as rat hippocampal brain slices.

In experiments of this kind, slices of hippocampus from a mammal, such as rat, are prepared and maintained in an interface chamber using conventional methods. Field EPSPs are recorded in the stratum radiatum of region CA1b and elicited by single stimulation pulses delivered once per 20 seconds to a bipolar electrode positioned in the Schaffer-commissural projections (see, Granger, R. et al., *Synapse*, 15:326–329 1993; Staubli, U. et al., 1994a, *Proc. Nat. Acad. Sci.*, 91:777–781; and Staubli, V. et al., 1994b, *Proc. Nat. Acad. Sci.*, 91:11158–11162; Arai, A. et al., 1994, *Brain Res.*, 638:343–346; Arai, A. et al., "Effects of a centrally active drug on AMPA receptor kinetics, submitted). The wave form of a normal EPSP is composed of an AMPA component, which has a relatively rapid rise time in the depolarizing direction (~5–10 msec) and which decays within ~20 msec.; an NMDA component (slow ~30–40 msec rise time and slow ~40–70 msec decay) (the NMDA portion will not appear in normal or artificial CSF (cerebro-spinal fluid) media, due to the voltage requirement for NMDA receptor channel activation, but in low magnesium media, an NMDA component may appear; a GABA (gamma-aminobutyric acid) component in the opposite (hyperpolarizing) direction as the glutamatergic (AMPA and NMDA) components, exhibiting a time course with a rise time of ~10–20 msec and very slow decay (~50–100 msec or more).

The different components can be separately measured to assay the effect of a putative AMPA receptor enhancing agent. This is accomplished by adding agents that block the unwanted components, so that the detectable responses are essentially only AMPA responses. For example, to measure AMPA responses, an NMDA receptor blocker (e.g., AP-5 or other NMDA blockers known in the art) and/or a GABA blocker (e.g., picrotoxin or other GABA blockers known in the art) are added to the slice. To prevent epileptiform activity in the GABA-blocked slices, known agents such as tetrodotoxin may be used.

AMPA upmodulators useful in the present invention are substances that cause an increased ion flux through the AMPA receptor complex channels in response to glutamatergic stimulation increased ion flux is typically measured as one or more of the following non-limiting parameters: at least a 10% increase in decay time, amplitude of the waveform and/or the area under the curve of the waveform and/or a decrease of at least 10% in rise time of the waveform, for example in preparations treated to block NMDA and GABA components. The increase or decrease is preferably at least 25–50%; most preferably it is at least 100%. How the increased ion flux is accomplished (e.g., increased amplitude or increased decay time) is of secondary importance; upmodulation is reflective of increased ion fluxes through the AMPA channels, however achieved.

An additional and more detailed assay is that of excised patches, i.e., membrane patches excised from cultured hippocampal slices; methods are described in Arai et al., 1994. Outside-out patches are obtained from pyramidal hippocampal neurons and transferred to a recording chamber. Glutamate pulses are applied and data are collected with a patch clamp amplifier and digitized (Arai et al., 1994). Because no GABA is applied to the patch, GABAergic currents will not be elicited. Any NMDA currents can be blocked as above (e.g., with AP-5).

The central action of a drug can be verified by measurement of field EPSPs in behaving animals (see, Staubli et al., 1994a) and time course of biodistribution can be ascertained via injection and subsequent quantitation of drug levels in various tissue samples. Quantitation can be accomplished by methods known to those skilled in the art and will vary depending on the chemical nature of the drug.

C. Other Compounds

The above described genus and species of compounds represent merely one example of glutamatergic compounds that may be used to treat sexual dysfunctions according to the present invention. The treatments provided by present invention are not limited to the compounds described above. The present invention also encompasses administering other compounds that enhance the stimulation of α-amino-3-hydroxy-5-methyl-isoxazole-4-propionic acid ("AMPA") receptors in a subject, said enhancement being sufficient to diminish the symptoms of sexual dysfunction. Examples of other such AMPA-selective compounds include 7-chloro-3-methyl-3–4-dihydro-2H-1,2,4 benzothiadiazine S,S, dioxide, as described in Zivkovic et al., 1995, *J. Pharmacol. Exp. Therap.*, 272:300–309; Thompson et al., 1995, *Proc. Nat. Acad. Sci. USA*, 92:7667–7671.

D. Subject Selection

Subjects contemplated for treatment in accordance with this invention include humans, laboratory animals, and domestic animals. It is generally understood that pharmacological treatments (e.g., administration of testosterone) influences sexual behavior in these animals.

The compounds and compositions described above are generally most useful to treat sexual dysfunctions in subjects having no demonstrable organic cause for the disorder. Conditions responsive to glutamatergic treatment include cases of reduced sexual drive, arousal or desire, age-associated hyposexuality unaccompanied by other physiological indications or by difficulties reaching orgasm.

Although certain conditions (e.g., some that arise from surgical interventions (e.g., for prostate conditions) and those diagnosed as vascular impotence (e.g., anatomic inability to achieve erection with intact psychological desire) are less likely to respond, the compounds and methods of the present invention are useful to treat individuals afflicted with physical disorders often also have psychogenic inhibitions that exacerbate the physical problem. Treatment of the psychogenic component with the methods of the present invention ameliorates the reduced sexual drive, arousal or desire, age-associated hyposexuality, and facilitates treatment of the physical component. Thus, even in cases of physical sexual dysfunction, combinations of hormone and physical treatments may be indicated.

E. Administration of Compounds

The compounds of this invention can be incorporated into a variety of formulations for therapeutic administration. Examples are capsules, tablets, syrups, suppositories, and various injectable forms. Administration of the compounds can be achieved in various ways, including oral, bucal, rectal, parenteral, intraperitoneal, intradermal, transdermal, etc., administration.

Preferred formulations of the compounds are oral preparations, particularly capsules or tablets containing each from about 1 milligram up to about 100 milligrams of active ingredient.

F. Dosage

The above described compounds and/or compositions are administered at a dosage that diminishes the symptoms of sexual dysfunction in subjects suffering from a sexual dysfunction while at the same time minimizing any side-effects. It is contemplated that the composition will be obtained and used under the guidance of a physician.

Typical dosages for systemic administration range from 0.1 to 1000 milligrams per kg weight of subject per administration. A typical dosage may be one 10–50 mg tablet taken once a day, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Dose levels can vary as a function of the specific compound, the severity of the symptoms, and the susceptibility of the subject to side effects. Some of the specific compounds that stimulate glutamatergic receptors are more potent than others. Preferred dosages for a given compound are readily determinable by those of skill in the art by a variety of means. A preferred means is to measure the physiological potency of a given compound that is a candidate for administration, by the method of Davis et al. (1996), submitted to Behavioral Neuroscience. Briefly, excised patches and excitatory synaptic responses are measured in the presence of different concentrations of test compounds, and the differences in dosage response potency are recorded and compared. Davis et al. found that one specific compound designated BDP-20 was about ten-fold more potent than another designated BDP-12 in a variety of behavioral (exploratory activity, speed of performance) and physical (excised patches and excitatory synaptic responses) tests. The relative physiological potency was an accurate measure of their behavioral potency. Thus, excised patches and excitatory synaptic responses may be used to gauge the relative physiological (and behavioral) potency of a given compound with regard to a known standard.

Preferred glutamatergic compounds for the treatment of sexual dysfunctions may have a half-life measured from less than 10 minutes to more than 2 hours. In some embodiments, the compound preferably has a rapid onset and short elimination half-life ($\leq 90$ min.).

EXAMPLES

The following examples are submitted for illustrative purposes only and should not be interpreted as limiting the invention in any way. A person of ordinary skill, with knowledge of this invention and of the prior art, will readily think of other subjects, other dysfunctions, and other glutamatergic substances that can be readily substituted in the following examples. Also, the patents and publications cited in this disclosure reflect the level of skill the art to which this invention pertains, and are herein individually incorporated by reference to the extent that they supplement, explain, provide a background for or teach methodology, techniques and/or compositions employed herein.

A. Preparation of Compound D1 (7-chloro-5-ethyl-3-methyl-3,4-dihydro-2H-1,2,4 benzothiadiazine S,S-dioxide)

1. Preparation of 5-chloro-3-ethyl-2-aminobenzenesulfonamide (D)

To a solution of 3-ethyl-2-aminobenzenesulfonamide (0.5043 g, 2.52 mmol) in 10 mL acetonitrile was added N-chlorosuccinimide (0.3163 g, 2.37 mmol). The mixture was stirred at reflux for 1 2.5 h, cooled, filtered, and concentrated in vacuo. Reaction was incomplete by $^1$H NMR; the purple solids were redissolved in acetonitrile and additional NCS (0.1019 g, 0.76 mmol) was added. The mixture was refluxed for 1 5 minutes and worked up as before. Column chromatography on the mixture of succinimide and D (40% ethyl acetate:hexanes) gave pure D (0.5224 g, 94%), m.p. 134–135° C. $^1$H NMR (300 MHz, DMSO): $\delta$7.45 (3H, s), 7.19 (1H, d, J=2.1 Hz), 5.76 (2H, s), 2.53 (2H, q, J=7.3 Hz), 1.14 (3H, i, J=7.3 HZ). $^{13}$C NMR (300 MHz, DMSO): $\delta$141.9, 131.8, 131.2, 125.4, 124.8, 118.1, 23.4, 12.7. FT-IR (KBr): 3457.8, 3427.9, 3358.4, 3268.9, 3080.1, 2970.8, 2364.5, 2334.7, 1630.6. 1556.1, 1541.2. 1451.7. 1312.6. 1188.3, 1148.6, 905.1, 875.3, 762.2, 611.3 cm$^{-1}$. HRMS: M$^+$ calculated=234.0230, found=234.0227.

2. Preparation of 7-chloro-5-ethyl-3-methyl-3,4-dihydro-2H-1,2,4 benzothiadiazine S,S-dioxide (D1)

To a 25 mL RB flask was added 5-chloro-3-ethyl-2-aminobenzenesulfonamide D (0.4074 g, 1.74 mmol), 8.5 mL acetonitrile, and 3Å molecular sieves. The stirring solution was cooled to 0° C. and acetaldehyde (0.15 mL, 2.68 mmol) and (±) 10-camphor sulphonic acid (catalytic) were added. After 1 h at 0° C., the reaction was filtered through Celite and solvent was removed to give crude D1. The light brown solid was dissolved in EtOAc, passed through silica, and concentrated to give pure D1 (0.4426 g, 98%), m.p. 181–183° C. $^1$H NMR (300 MHz, DMSO): $\delta$7.70 (1H, d, J=11.8 Hz), 7.35 (1H, d, J=2.2 Hz), 7.21 (1H, d, J=2.2 Hz), 6.24 (1H, s), 4.80 (1H, m), 2.52 (2H, m), 1.48 (3H, d, 7.1 Hz), 1.13 (3H, t, J=7.4 Hz). $^{13}$C NMR (500 MHz, DMS0): $\delta$140.2, 132.4, 131.1, 122.2, 120.5, 120.0, 62.2, 23.2, 20.1, 12.7. FT-IR (KBr): 3405.9, 3232.5, 3001.5, 2942.7, 2884.0, 1490.5, 1438.5, 1309.6, 1282.4, 1160.2, 1140.1, 864,5, 743.8, 718.0, 567.5 cm$^{-1}$. HRMS: M$^+$ calculated=260.0386, found=260.0386.

Those of skill in the art will readily appreciate that the foregoing protocol can be used, with only minor modifications, to prepare the other compounds of the present invention.

B. Administration of AMPA-kines to Rats

Rats and mice have traditionally been the quintessential test animals for developing animal models for treating disease. A large body of studies indicates that hormones and treatments that modulate sexual behavior in rodents also do so in other mammals, humans included.

In the male rat, "age-related sexual dysfunctions" or deficits of sexual arousal/motivation occur as early as one year of age. This form of sexual deficit is apparently not reversible by administration of exogenous testosterone (Gray et al., 1981).

Although early studies indicated the possibility of differences in plasma levels of testosterone in old mating versus non-mating males, subsequent batteries of experiments have failed to replicate these initial findings, and indicate that decline in testosterone is unlikely to be the primary cause of sexual dysfunction with increasing age (Smith et al., 1992). It seems probable that the major alterations responsible for the age-related changes in behavior reside in the CNS, and these are likely to be non-hormone dependent.

Central glumatergic enhancement has been shown to have positive effects on age-related declines in learning (Granger et al., 1996). We undertook experiments to test whether central glutamatergic enhancement would also affect age-related declines in sexual performance.

Two of the primary characteristics of sexual deficit in aged rats are those of delay. Both latency to intromit and latency to ejaculate are significantly lengthened with increasing age (Smith and Davidson, 1990; Smith et al., 1992).

Figure 1:
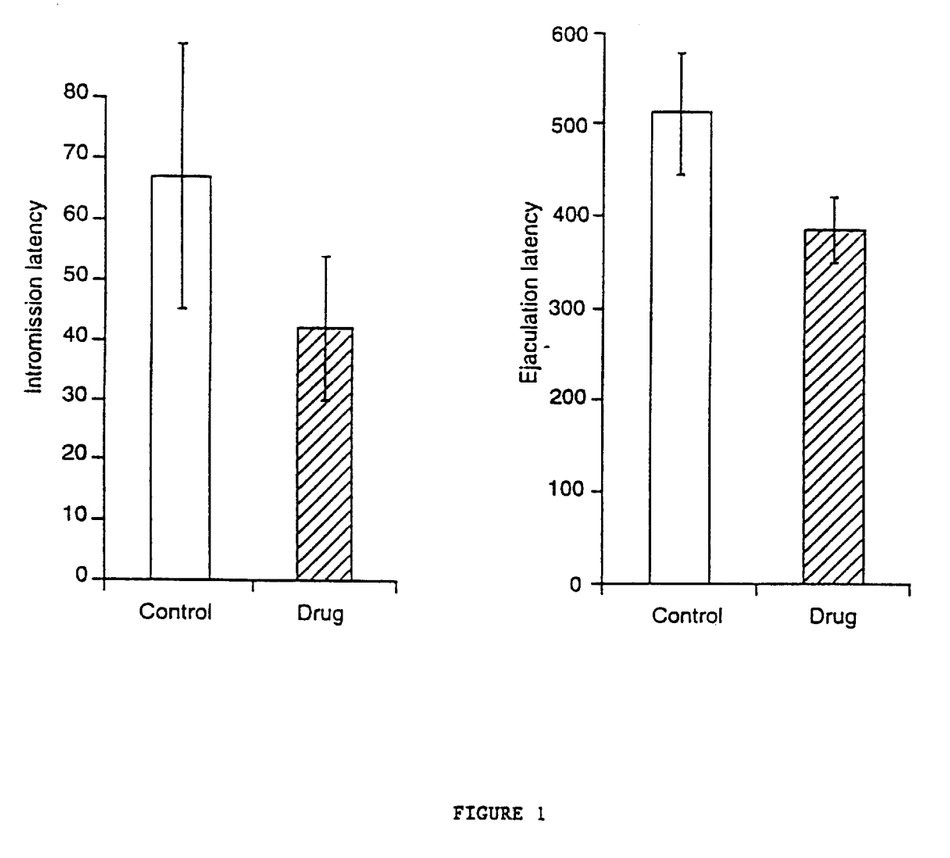
FIG. 1 compares intromission and ejaculatory latency in aged rats treated with glutamatergic enhancers, as compared to control rats.

In the present experiments, aged (16–18 months) male Long-Evans rats (n=9) were paired with receptive females for 30-minute periods once a week for two months, 30 minutes after receiving injections of either saline or a centrally-active glutamatergic enhancer. On the days that they received the drug, animals exhibited significantly decreased latencies to intromit (IL) and to ejaculate (EL) as compared with their performance on control days. FIG. 1 shows the means and standard errors for IL ($p<0.05$ by the Wilcoxon test) and EL ($p<0.03$ by the Wilcoxon test) on control (white) and drug (striped) days for a set of nine animals.

The observed changes in IL and EL with the glutamatergic enhancer are thus consistent with amelioration of age-related sexual impairment, suggesting that central glutamatergic enhancement may serve as a novel treatment for this condition.

C. Administration to Humans

As mentioned above, not all sexual dysfunctions are treated with the compounds used herein. Thus, a first step in treating humans is generally determining which individuals have dysfunctions which are likely to respond (e.g., neurogenic, psychogenic or age-related sexual dysfunctions), and which will not.

Determination whether a subject is suffering from a sexual dysfunction that is substantially neurogenic or psychogenic in origin is made by a person skilled in the art using a number of readily available diagnostic procedures. In general, the presence of typical DSMIII sexual dysfunctions in humans can be ascertained via questionnaires or interviews. Spontaneous self-identification by individuals of a low or comparatively diminished desire or ability to function sexually and to experience sexual pleasure is one criterion for selecting individuals to be treated. Few laboratory tests are required for the routine evaluation of common sexual complaints (Kligman, 1991). Impotence which is a side-effect of drugs such as beta-blockers or alcohol is deemed to be neurogenic impotence in the present specification.

Although the psychosexual history of the subject may be the only criterion used to select candidates for treatment, it may be desirable to also rule out purely physical conditions that are not treatable with the compounds of the invention should be ruled out.

1. Diagnosis of Dysfunctions that are Substantially only Neurogenic or Psychogenic in Origin A subject suffering from impotence can be given a physical examination with particular attention to possible penile and scrotal pathology precluding an erection sufficient for vaginal penetration. Such tests include determination of the penobrachial blood pressure index (PBPI), Doppler investigation of the penile arteries, and a papaverine test. The subject may further be tested for signs of penile venous leakage or atherosclerosis.

The PBPI is the penile systolic blood pressure divided by the systolic blood pressure determined at one of the arms. These blood pressures can be determined by any numerous standard techniques. Thus, the penile systolic blood pressure can be determined by placing around the base of the free part of the penis in the flaccid state, an inflatable cuff, which is capable of being used to apply variable pressure, readable from a gauge, to an object around which the cuff is placed, localizing the penile arteries with a Doppler ultrasound probe (e.g., and 8 MHz probe, such as the Mini Doplex D500™ available from Huntleigh Technology, Luton, United Kingdom), and then inflating and deflating the cuff and ascertaining the pressure at which the Doppler sound reappears. The pressure at which the Doppler sound reappears is the penile systolic blood pressure. A male's penile blood pressure is regarded as normal if his PBPI is>0.80.

With regard to Doppler investigation, each of the two penile cavernous arteries is investigated distal to the aforementioned cuff using Doppler ultrasound. The function of each of the two arteries is assessed by Doppler ultrasound using an arbitrary scale of 0, 1, 2 or 3, where 0 means that the function is so deficient that the artery cannot be located and 3 means that the artery is well enough that maximal Doppler sound is observed.

In the papaverine test, a tourniquet is placed at the base of the free part of the penis and tightened and then, with the patient seated, 30 mg of papaverine in 1 ml of a physiologically acceptable fluid such as physiological saline or phosphate-buffered saline is injected into the penile cavernous body. (In persons suspected of having impotence due to a suprasacral nerve lesion or a psychogenic dysfunction, only 15 mg of papaverine is administered, because of the high incidence of papaverine-induced priapism in such cases.) Five minutes after the injection, the tourniquet is removed and an ultrasound Doppler investigation of the penile cavernous arteries is carried out as described above. The function of the arteries is regarded as normal if both of them score a 3 on the arbitrary scale. After the Doppler investigation, penile vibration, at about a 4 Hz with an amplitude of about 1.2 mm (carried out with, e.g., a Vibrector™ from Multicept, Gentofte, Denmark) is performed out for five to ten minutes and then erectile response is evaluated. Erectile response is classified as full rigidity, if the angle between the penis and the legs in the standing position is >90°, and tumescence or no response if the angle is less than or equal to 45°. The papaverine employed in the "papaverine test" described above could be replace with VIP (approximately 50 g).

An impotent male who does not have an anatomical deficiency that would preclude having an erection sufficient for vaginal penetration, who has a PBPI>0.80, who scores of 2 or 3 in Doppler ultrasound investigations of both of the cavernous arteries of the penis after papaverine injection as described above, and who has a fully rigid erection after papaverine injection and vibration as described above, is suffering from neurogenic or psychogenic dysfunction.

Generally, a male with a PBPI less than about 0.60, with scores of 0 in Doppler investigations of both penile cavernous arteries (after papaverine injection as described above), and with a less than fully rigid erection after papaverine injection and vibration will have impotence caused by "untreatable" atherosclerosis.

Whether a subject suffers from impotence that is untreatable because of venous leakage may be determined by a number of methods. One method is cavernosometry, optionally supplemented with cavernosography. See, e.g., Delcour et al. (1986) *Radiology* 161:799; Porst et al. (1987) *J. Urol.* 137: 1163; Lue et al. (1987) *J. Urol.* 37: 829. Cavernosometry can be performed using, both before and after intracavernosal injection of 60 mg of papaverine (in 1 ml of physiological saline), infusion of physiological saline through a 19-gauge needle into one corpus cavernosum with a 21-gauge needle inserted into the other corpus cavernosum for measurement of intracorporal pressure (which is recorded on a plotter). The infusion rates needed to induce and maintain an erection are measure. If the infusion rate needed to maintain an erection is greater than 50 ml/min before administration of the papaverine and greater than 15 ml/min after administration of the papaverine, untreatable venous leakage is present. As long as an erection can be achieved at some flow rate less than about 100 ml/min before injection of the papaverine and less than about 50 ml/min after the injection of papaverine, it might be possible, using cavernosography, to locate the venous lesion associated with the leakage, and thereby confirm the diagnosis based on cavernosometry and provide information for possible surgical correction for the leakage. In the cavernosography, the penis is X-rayed, both before and after intracavernosal injection of 60 mg papaverine in 1 ml of physiological saline, while infusing contrast medium into the corpus cavernosum (e.g., through a 19-gauge needle) at a flow rate that maintains an erection during the x-raying. Numerous contrast media suitable for the procedure are available in the art; these are typically aqueous solutions of iodinated compounds that provide between about 180 mg/ml and about 360 mg/ml of iodine. Examples are Omnipaque $_{240}$™, which is a solution of iohexol providing 240 mg/ml of iodine sold by Winthrop Pharmaceuticals, New York, N.Y., USA, and Iopamiro (Registered™), which is a solution of iopamidol providing 300 mg/ml iodine sold by Astra Meditec, Goteborg, Sweden. Typically 50–100 ml of the contrast medium will be employed for each x-ray (i.e., before and then after the injection of papaverine). In the cavernosometry and cavernosography, 30 mg papaverine (in 1 ml physiological saline) coupled with stimulation by vibration can be employed in place of 60 mg papaverine (in 1 ml physiological saline).

2. Assessing Progress of the Treatment

The success of treatment is measured by monitoring and recording the nature, number, frequency and duration of instances of sexual stimulation and sexual behavior. The sexual behavior to be monitored can comprise sexual relations between the patient and another person or can involve sexual behaviors that do not involve another person. Sexual responsiveness may be induced and gauged by: touching or erotically manipulating erogenous areas of the genital organs or other erogenous parts of the body; providing visual stimulation, as with a sexually explicit film or other form of sexually stimulating show or display; or providing vibratory stimulation to the penis (for example, by resting the penis on the table of a vibrating apparatus such as that of a Vibrector system (Multicept, Genofte, Denmark), at between about 30 Hz and about 100 Hz with an amplitude of about 1 to about 5 mm), alone or in combination. A preferred method of sexual stimulation includes providing visual stimulation, as with a sexually explicit film, simultaneously with vibratory stimulation of the penis, as with a Vibrector system set to between about 30 Hz and about 60 Hz (usually about 50 Hz) in frequency and between about 1 mm and about 2.5 mm (usually about 2.2 mm) in amplitude.

The progress of the treatment is monitored by having the patient record instances and frequency of sexual behavior or of subjective sexual arousal, for example by keeping a diary. In addition, the supervising physician will maintain a log of treatments and observations. In combination, the diary and log will allow for a comparison of instances and frequency of sexual behavior or of subjective sexual arousal before and in response to treatment.

D. Kits

In addition, the present invention provides for kits with unit doses of AMPA up-modulating drugs either in oral or injectable doses. In addition to the containers containing the unit doses will be a informational package insert describing the use and attendant benefits of the drugs in treating neurodegenerative pathologies not significantly affecting memory or learning. Preferred compounds and unit doses are those described herein above.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

We claim:

1. A method for treating a sexual dysfunction in a subject, said method comprising administering an effective amount of a compound that enhances the stimulation of α-amino-3-hydroxy-5-methyl-isoxazole-4-propionic acid ("AMPA") receptors in said subject, said enhancement being sufficient to diminish the symptoms of sexual dysfunction.

2. The method of claim 1 wherein the AMPA receptors are present in the central nervous system.

3. The method of claim 1 wherein the drugs are administered orally.

4. The method of claim 1 wherein the drugs are administered by injection.

5. A method of increasing sexual activity in males suffering from age-related sexual dysfunctions that may be treated with glutamatergic enhancers, comprising administering a compound of claim 1 to said subject in an amount sufficient to diminish the symptoms of sexual dysfunction.

6. A kit, comprising a container containing the composition of claim 1 and instructions for using the composition for treating sexual dysfunction in a subject.

7. A method in accordance with claim 1 comprising pharmacologically amplifying said natural stimulators by administering to said subject an effective amount of a compound having the following formula, with ring vertices numbered as shown:

in which:

$R^1$ is a member selected from the group consisting of N and CH;

m is 0 or 1;

$R^2$ is a member selected from the group consisting of $(CR^8{}_2)_{n-m}$ and $C_{n-m}R^8{}_{2(n-m)-2}$, in which n is 4, 5, 6, or 7, the $R^8$'s in any single compound being the same or different, each $R^8$ being a member selected from the group consisting of H and $C_1$–$C_6$ alkyl, or one $R^8$ being combined with either $R^3$ or $R^7$ to form a single bond linking the number 3' ring vertex to either the number 2 or the number 6 ring vertices or a single divalent linking moiety linking the number 3' ring vertex to either the no. 2 or the no. 6 ring vertices, the linking moiety being a member selected from the group consisting of $CH_2$, $CH_2$—$CH_2$, CH=CH, O, NH, N($C_1$–$C_6$ alkyl), N=CH, N=C($C_1$–$C_6$ alkyl), C(O), O—C(O), C(O)—O, CH(OH), NH—C(O), and N($C_1$–$C_6$ alkyl)—C(O);

$R^3$, when not combined with any $R^8$, is a member selected from the group consisting of H, $C_1$–$C_6$ alkyl, and $C_1$–$C_6$ alkoxy;

$R^4$ is either combined with $R^5$ or is a member selected from the group consisting of H, OH, and $C_1$–$C_6$ alkoxy;

$R^5$ is either combined with $R^4$ or is a member selected from the group consisting of H, OH, $C_1$–$C_6$ alkoxy, amino, mono($C_1$–$C_6$ alkyl)amino, di($C_1$–$C_6$ alkyl) amino, and $CH_2OR^9$, in which $R^9$ is a member selected from the group consisting of H, $C_1$–$C_6$ alkyl, an aromatic carbocyclic moiety, an aromatic heterocyclic moiety, an aromatic carbocyclic alkyl moiety, an aromatic heterocyclic alkyl moiety, and any such moiety substituted with one or more members selected from the group consisting of $C_1$–$C_3$ alkyl, $C_1$–$C_3$ alkoxy, hydroxy, halo, amino, alkylamino, dialkylamino, and methylenedioxy;

$R^6$ is either H or $CH_2OR^9$;

$R^4$ and $R^5$ when combined form a member selected from the group consisting of in which:
$R^{10}$ is a member selected from the group consisting of O, NH and N($C_1$–$C_6$ alkyl);
$R^{11}$ is a member selected from the group consisting of O, NH and N($C_1$–$C_6$ alkyl);
$R^{12}$ is a member selected from the group consisting of H and $C_1$–$C_6$ alkyl, and when two or more $R^{12}$'s are present in a single compound, such $R^{12}$'s are the same or different;
p is 1, 2, or 3; and
q is 1 or 2; and $R^7$, when not combined with any $R^8$, is a member selected from the group consisting of H, $C_1$–$C_6$ alkyl, and $C_1$–$C_6$ alkoxy.

8. A method in accordance with claim 7 in which $R^2$ is a member selected from the group consisting of $(CHR^8)_{n-m}$ and $C_{n-m}HR^8{}_{2(n-m)-3}$, and $R^3$ is a member selected from the group consisting of H, $C_1$–$C_6$ alkyl, and $C_1$–$C_6$ alkoxy.

9. A method in accordance with claim 7 in which $R^2$ is a member selected from the group consisting of $(CHR^8)_{n-m}$ and $C_{n-m}HR^8{}_{2(n-m)-3}$, and one $R^8$ is combined with either $R^3$ or $R^7$ to form a single bond linking the number 3' ring vertex to either the number 2 or the number 6 ring vertices or a single divalent linking moiety linking the number 3' ring vertex to either the number 2 or the number 6 ring vertices, the linking moiety being a member selected from the group consisting of $CH_2$, $CH_2$—$CH_2$, CH=CH, O, NH, N($C_1$–$C_6$ alkyl), N=CH, N=C($C_1$–$C_6$ alkyl), C(O), O—C(O), C(O)—O, CH(OH), NH—C(O), and N($C_1$–$C_6$ alkyl)—C(O).

10. A method in accordance with claim 7 in which $R^2$ is a member selected from the group consisting of $(CHR^8)_{n-m}$ and $C_{n-m}HR^8{}_{2(n-m)-3}$, and one $R^8$ is combined with either $R^3$ or $R^7$ to form a single bond linking the number 3' ring vertex to either the number 2 or the number 6 ring vertices or a single divalent linking moiety linking the number 3' ring vertex to either the number 2 or the number 6 ring vertices, the linking moiety being a member selected from the group consisting of $CH_2$, $CH_2$—$CH_2$, CH=CH, O, NH, C(O), and CH(OH).

11. A method in accordance with claim 7 in which $R^2$ is a member selected from the group consisting of $(CHR^8)_{n-m}$ and $C_{n-m}HR^8{}_{2(n-m)-3}$, and one $R^8$ is combined with either $R^3$ or $R^7$ to form a single divalent linking moiety linking the number 3' ring vertex to either the number 2 or the number 6 ring vertices, the linking moiety being a member selected from the group consisting of $CH_2$, O, NH, C(O), and CH(OH).

12. A method in accordance with claim 7 in which m is zero, $R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, NH, C(O), and CH(OH).

13. A method in accordance with claim 7 in which m is zero, $R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, and NH.

14. A method in accordance with claim 7 in which $R^4$ and $R^5$ are combined to form a member selected from the group consisting of 15. A method in accordance with claim 14 in which $R^{12}$ is a member selected from the group consisting of H and $CH_3$.

16. A method in accordance with claim 7 in which $R^4$ and $R^5$ are combined to form a member selected from the group consisting of in which $R^{12}$ is a member selected from the group consisting of H and $CH_3$.

17. A method in accordance with claim 7 in which:

m is zero;

$R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, NH, C(O), and CH(OH);

$R^4$ and $R^5$ are combined to form a member selected from the group consisting of $R^{10}$ is O;

$R^{11}$ is O;

$R^{12}$ is a member selected from the group consisting of H and $CH_3$.

18. A method in accordance with claim 7 in which $R^4$ and $R^5$ are combined to form a member selected from the group consisting of in which $R^{10}$ is O, $R^{11}$ is O, and $R^{12}$ is a member selected from the group consisting of H and $CH_3$.

19. A method in accordance with claim 7 in which:

m is zero;

$R^2$ is a member selected from the group consisting of $CHR^8$—$CH_2$—$CH_2$—$CH_2$ and $CHR^8$—$CH_2$—$CH_2$—$CH_2$—$CH_2$, in which $R^8$ is combined with $R^7$ to form a single divalent linking moiety linking the 2 and 3' ring vertices, the linking moiety being a member selected from the group consisting of $CH_2$, O, and NH;

$R^4$ and $R^5$ are combined to form a member selected from the group consisting of $R^{10}$ is O;

$R^{11}$ is O; and $R^{12}$ is a member selected from the group consisting of H and $CH_3$.

20. A method in accordance with claim 7 in which:

m is zero;

$R^1$ is N;

$R^2$ is $CHR^8$—$CH_2$—$CH_2$—$CH_2$;

$R^3$ is H;

$R^3$ is H;

$R^4$ and $R^5$ are combined to form $R^6$ is H;

$R^8$ is combined with $R^7$ to form a single O atom linking the 2 and 3' ring vertices; and $R^{12}$ is H.

21. A method in accordance with claim 1 comprising pharmacologically amplifying said natural stimulators by administering to said subject an effective amount of a compound having the following formula, with ring vertices numbered as shown:

in which:

$R^{21}$ is a member selected from the group consisting of H, halo and $CF_3$;

$R^{22}$ and $R^{23}$ either are both H or are combined to form a double bond bridging the 3 and 4 ring vertices;

$R^{24}$ is a member selected from the group consisting of H, $C_1$–$C_6$ alkyl, $C_5$–$C_7$ cycloalkyl, $C_5$–$C_7$ cycloalkenyl, Ph, $CH_2Ph$, $CH_2SCH_2Ph$, $CH_2X$, $CHX_2$, $CH_2SCH_2CF_3$, $CH_2SCH_2CH$=$CH_2$, and where Ph is phenyl and X is halo; and

$R^{25}$ is a member selected from the group consisting of H and $C_1$–$C_6$ alkyl.

22. A method in accordance with claim 21 in which:

$R^{21}$ is a member selected from the group consisting of Cl and $CF_3$;

$R^{22}$ and $R^{23}$ either are both H or are combined to form a double bond bridging the 3 and 4 ring vertices;

$R^{24}$ is a member selected from the group consisting of H, $CH_2CH(CH_3)_2$, cyclohexyl, cyclohexenyl, Ph, $CH_2Ph$, $CH_2SCH_2Ph$, $CH_2Cl$, $CHCl_2$, $CH_2SCH_2CF_3$, $CH_2SCH_2CH$=$CH_2$, and where Ph is phenyl; and

$R^{25}$ is a member selected from the group consisting of H and $CH_3$.

23. A method in accordance with claim 21 in which:

$R^{21}$ is Cl;

$R^{22}$ and $R^{23}$ are both H;

$R^{24}$ is a member selected from the group consisting of cyclohexyl, cyclohexenyl, Ph, $CH_2Ph$, $CH_2SCH_2Ph$, and where Ph is phenyl; and $R^{25}$ is H.

24. A method in accordance with claim 21 in which said compound is

25. A method in accordance with claim 21 in which said compound is

26. A method in accordance with claim 21 in which said compound is

27. A method in accordance with claim 21 in which said compound is

28. A method of claim 7, wherein said compound has the following structure:

29. The method of claim 7 wherein the AMPA receptors are present in the central nervous system.

30. The method of claim 7 wherein the drugs are administered orally.

31. The method of claim 7 wherein the drugs are administered by injection.

32. A method of increasing sexual activity in males suffering from age-related sexual dysfunctions that may be treated with glutamatergic enhancers, comprising administering a compound of claim 7 to said subject in an amount sufficient to diminish the symptoms of sexual dysfunction.

33. A kit, comprising a container containing the composition of claim 7 and instructions for using the composition for treating sexual dysfunction in a subject.

* * * * *